United States Patent
Ott

(10) Patent No.: US 11,479,522 B2
(45) Date of Patent: Oct. 25, 2022

(54) METHOD FOR THE PURIFICATION OF ALKANES

(71) Applicant: BASF SE, Ludwigshafen am Rhein (DE)

(72) Inventor: Timo Ott, Duisburg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/441,210

(22) PCT Filed: Mar. 17, 2020

(86) PCT No.: PCT/EP2020/057248
§ 371 (c)(1),
(2) Date: Sep. 20, 2021

(87) PCT Pub. No.: WO2020/187894
PCT Pub. Date: Sep. 24, 2020

(65) Prior Publication Data
US 2022/0153662 A1    May 19, 2022

(30) Foreign Application Priority Data
Mar. 21, 2019   (EP) .................................. 19164427

(51) Int. Cl.
C07C 7/14    (2006.01)
C07C 7/17    (2006.01)
C10L 3/10    (2006.01)

(52) U.S. Cl.
CPC ................ *C07C 7/17* (2013.01); *C10L 3/101* (2013.01); *C10L 2290/545* (2013.01)

(58) Field of Classification Search
None
See application file for complete search history.

(56) References Cited

U.S. PATENT DOCUMENTS

| | | | |
|---|---|---|---|
| 4,666,468 A * | 5/1987 | Wu ...................... | B01D 53/228 95/47 |
| 5,354,545 A * | 10/1994 | Buisman ................ | C12M 21/04 423/576.2 |
| 2008/0161591 A1 * | 7/2008 | Richards ................. | C07C 29/00 558/44 |

(Continued)

FOREIGN PATENT DOCUMENTS

| | | |
|---|---|---|
| EP | 3071549 B1 | 10/2017 |
| WO | 2015/071365 A1 | 5/2015 |

(Continued)

OTHER PUBLICATIONS

European Search Report for EP Patent Application No. 19164427.7, dated Jun. 28, 2019, 3 pages.

(Continued)

*Primary Examiner* — Tam M Nguyen
(74) *Attorney, Agent, or Firm* — ArentFox Schiff LLP

(57) ABSTRACT

The present invention relates to a method for the purification of alkanes, especially methane, wherein an alkane comprising impurities, especially methane, is reacted with an active compound, optionally in the presence of sulfur trioxide, whereby the impurities are removed. The present invention furthermore relates to the use of the active compound and sulfur trioxide in the purification of alkanes, especially methane.

11 Claims, 1 Drawing Sheet

Batch or Continous Reactor or Reactor-Cascade with or without recirculation of gas suitable for gas-mixing.

(56) References Cited

U.S. PATENT DOCUMENTS

2016/0289181 A1\* 10/2016 Ott .................... C07C 407/00
2019/0270701 A1\* 9/2019 Ott .................... C07C 409/44
2021/0070700 A1\* 3/2021 Ott .................... C07C 303/06
2022/0033354 A1\* 2/2022 Ott .................... C07C 303/06

FOREIGN PATENT DOCUMENTS

| WO | 2015/071455 A1 | 5/2015 |
| WO | 2018/096138 A1 | 5/2018 |
| WO | 2018/146153 A1 | 8/2018 |
| WO | 2019/036698 A1 | 2/2019 |
| WO | 2019/158577 A1 | 8/2019 |
| WO | 2020/064466 A1 | 4/2020 |
| WO | 2020/064573 A1 | 4/2020 |

OTHER PUBLICATIONS

International Search Report for PCT Patent Application No. PCT/EP2020/057248, dated Apr. 30, 2020, 3 pages.

\* cited by examiner

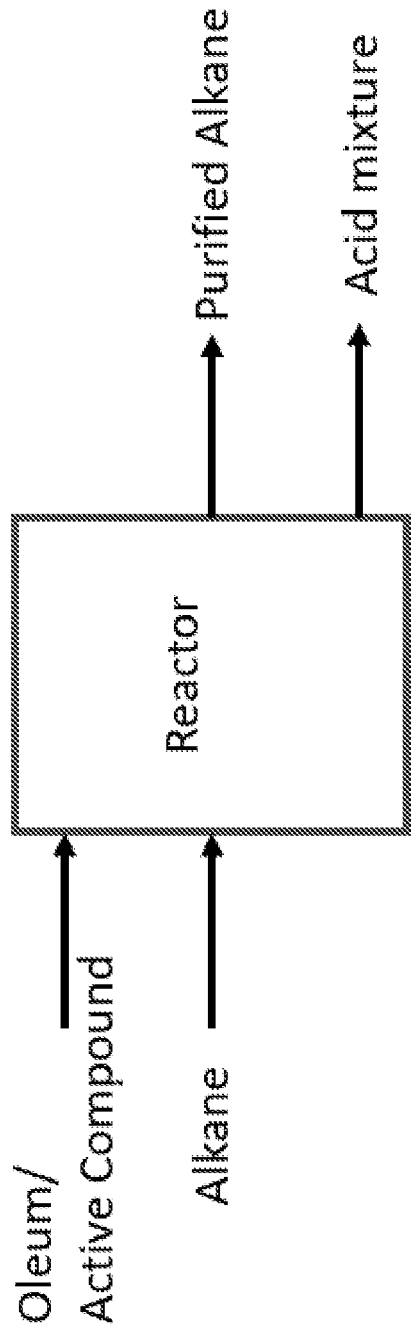

METHOD FOR THE PURIFICATION OF ALKANES

CROSS-REFERENCE TO RELATED APPLICATIONS

This application is a National Stage Entry of PCT/EP2020/057248, filed Mar. 17, 2020, which claims priority to EP application No. 19164427.7 filed Mar. 21, 2019, the disclosures of each of which are hereby incorporated by reference in their entirety.

The present invention relates to a method for the purification of alkanes, especially methane, wherein an alkane comprising impurities, especially methane, is reacted with an active compound, optionally in the presence of sulfur trioxide, whereby the impurities are removed. The present invention furthermore relates to the use of the active compound and the use of sulfur trioxide in the purification of alkanes, especially methane.

Alkanes form a basic group of organic compounds and are used in a variety of processes and applications. The simplest representative of alkanes is methane. Although the largest amount of alkanes is used as fossil fuels for the generation of energy, alkanes, and particularly methane, are also important basic materials for chemical syntheses. Methane, which is a main component of natural gas, is for example reacted with water in steam reforming processes in order to obtain synthesis gas, i.e., carbon monoxide and hydrogen, and is thus used as a principal carbon source.

Alkanes are typically obtained from fossil resources, such as natural gas, crude oil or the like. They may be separated and purified in large-scale industrial processes, for example in refineries. Although thus obtained alkanes, and particularly methane, have some level of purity, they may still comprise significant amounts of impurities. For some applications, however, highly purified alkanes, and particularly highly purified methane, are required.

In the current state of the art, methane is typically purified by cryogenic distillation methods. Furthermore, pressure swing adsorption (PSA) and membrane technologies have been developed. All of these technologies require a compromise between purity, complexity and energy usage.

For example, WO 2019/036698 A1 discloses a method for extracting hydrocarbons by a sequence of process steps involving (i) generating sulfur trioxide, (ii) delivering the sulfur trioxide to a deposit containing a clathrate hydrated to generate a hydrocarbon, and (iii) recovering the hydrocarbon.

High-Purity methane (>99.98%) is required in considerable amounts for the chlorination of methane, i.e., the production of chloromethane, e.g., methyl chloride, chloroform, and methylene chloride. Furthermore, ultra-high-purity methane (>99.9995%) is, for example, used as a carbon source in the production of high-purity carbon black (for electronics), carbide tools, photoreceptor drums, and amorphous silicon solar cells. It is also required in the fields of leading-edge technologies such as ceramics and diamond thin film as a pure carbon source, for advanced gas cooled nuclear reactors (AGR). Furthermore, ultra-high-purity methane may be used as a calibration gas. Growing demand and an expanding market are expected in the future.

The commercial standard for ultra-high-purity methane is a purity of 99.9995%.

There is therefore a need for methods for the purification of alkanes and particularly methane, which affords the aforementioned high-purity and ultra-high-purity grades, which is simple and cost-efficient and which desirably allows for purity grades above the aforementioned commercial standard of 99.9995%.

It is thus an object of the invention to provide such a method for the purification of alkanes. Particularly, a method for the purification of methane is to be provided. Purification in the sense of the present invention particularly refers to the removal of higher alkane compounds from an alkane to be purified.

In a first embodiment, the object of the invention is solved by a method for the purification of alkanes, especially methane, wherein an impure alkane, especially methane, is contacted with an active compound comprising a heterolytically cleavable bond between two atoms, each selected from the group consisting of nitrogen, phosphorus, sulphur and oxygen.

In a preferred embodiment, the impure alkane, especially methane is contacted with the active compound in the presence of sulfur trioxide.

The term impure alkane within the sense of the present invention refers to a mixture of an alkane with impurities, wherein the desired alkane accounts for less than 99.99 wt % or less than 99.99 vol % of the respective mixture. Particularly, alkanes with a higher carbon number than the desired alkane are considered impurities according to the present invention. The desired alkane may account for less than 99 wt % or 99 vol % of the respective mixture, for less than 95 wt % or 95 vol % of the respective mixture or even for less than 90 wt % or 90 vol % of the respective mixture. The desired alkane preferably accounts for at least 50 wt % or 50 vol %, especially at least 60 wt % or 60 vol %, preferably at least 70 wt % or 70 vol %, preferred at least 80 wt % or 80 vol % and particularly at least 85 wt % or 85 vol % of the respective mixture.

The impure alkane preferably has a low nitrogen content. Impurities in the sense of the present invention may, in addition to higher alkanes, comprise further compounds, which are removed by the method of the present invention. A particular example is tetrahydrothiophen, which may also be removed.

Higher alkanes or alkanes with a higher carbon number within the meaning of the present application are alkanes with 2 to 10 carbon atoms, preferably alkanes with 2 to 5 carbon atoms.

In a preferred embodiment of the invention, the impure alkane is an impure methane. The impure methane is particularly a gaseous mixture of methane with other higher alkanes, especially a mixture of methane with ethane and/or propane. Methane may account for less than 99.99 vol % of the mixture, or even less than 99 vol %, less than 95 vol % or less than 90 vol %. Besides ethane and/or propane, further higher alkanes may be present as impurities within the sense of the present invention. For example, an impure methane may comprise at least 0.001 vol % of ethane gas, preferably it comprises 0.01 vol % or less of ethane, especially 0.1 vol % or 1 vol. % or less. But even if the content of ethane is 5% or 10%, the method according to the present invention is applicable.

The impure alkane is preferably in a gaseous state at room temperature. Particularly, if an impure methane is employed, the alkane is in a gaseous state at room temperature. The method is preferably performed in a high-pressure-reactor and particularly the reactor is pressured with methane gas.

The method of the present invention comprises in one preferred embodiment the following steps:
1) Synthesis of an active compound,
2) Providing the alkane to be purified and optionally $SO_3$,
3) Reaction of the alkane to be purified with the active compound, optionally in the presence of $SO_3$,
4) Removing the purified alkane from the reactor.

In an especially preferred embodiment, the alkane is methane and the method comprises the following steps:
1) Synthesis of an active compound,
2) Providing methane to be purified and optionally $SO_3$,
3) Reaction of the methane with the active compound, optionally in the presence of $SO_3$,
4) Removing the purified methane from the reactor.

The alkane in step 4 has a higher degree of purity compared to the beginning of the reaction. A higher degree of purity here particularly refers to a lower amount of higher alkane impurities being present in the recovered alkane. Especially, when methane gas is employed, the methane gas recovered from the reaction has a higher concentration of pure methane and a lower concentration of impurities, particularly higher alkane impurities and more particularly ethane and/or propane, than the methane gas originally employed.

In a preferred embodiment, the impure alkane, especially methane is contacted with the active compound in the presence of sulfur trioxide.

In the prior art, it is generally described that any alkane may be reacted with sulfur trioxide in the presence of an initiator in order to form alkanesulfonic acids. It is believed the initiator reacts with sulfur trioxide ($SO_3$) and forms an activated form of sulfur trioxide ($SO_3^\#$), which then reacts with the alkane to afford the corresponding alkanesulfonic acid. Surprisingly it has been found that the initiators employed in the aforementioned processes may be used as active compounds in the purification of alkanes according to the present invention.

Without the intention of being bound by theory, it is believed that the formation of alkanesulfonic acids may proceed faster for alkanes with a higher carbon number than for alkanes with a lower carbon number. Accordingly, impurities present in an impure alkane to be purified preferentially react with the activated form of sulfur trioxide (active compound according to the present invention) in comparison with the alkane to be purified and the concentration of the desired alkane is thus increased. The alkanesulfonic acids formed from the impurities can be easily separated from the desired alkane.

For example, if impure methane ($CH_4$) comprising higher alkane impurities ($C_nH_{2n+2}$, n=2,3, . . . ) is employed, the following reactions are considered to take place

$$CH_4 + SO_3^\# \rightarrow H_3C\text{—}SO_3H \quad (R1)$$

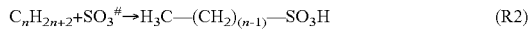
$$C_nH_{2n+2} + SO_3^\# \rightarrow H_3C\text{—}(CH_2)_{(n-1)}\text{—}SO_3H \quad (R2)$$

and it is believed that reaction R2 proceeds faster than reaction R1. Accordingly, the impure methane gas, which is contacted with the activated form of sulfur trioxide (active compound according to the present invention), is enriched in methane, because a higher amount of higher alkane impurities than of methane is consumed. The same principle applies to other alkanes than methane, which may be purified and freed of higher alkanes in a similar fashion.

At the same time, alkanesulfonic acids are produced as a side product. Those alkanesulfonic acids can easily be separated from the gaseous methane as they are not gaseous under standard conditions. Since the impure methane still primarily comprises methane, the main side product is methanesulfonic acid, which is itself a desirable and valuable chemical. Therefore, the methanesulfonic acid obtained as a side-product may be isolated. Particularly, the inventive method can be employed in combination with a method for producing alkanesulfonic acids, especially methanesulfonic acid. Thus, in a simple and efficient process, both purified methane and methanesulfonic acid may be produced.

Sulfur trioxide may be used in a form of oleum with a trioxide content of 50% (w/w) or less, or 65% (w/w) or more. It has been found that oleum with a sulfur trioxide content of 65 (w/w) or more, especially of 70% w/w or more can be used without negatively affecting the inventive process. Even pure sulfur trioxide (100% (w/w) sulfur trioxide) may be used.

Sulfur trioxide is, if at all, preferably employed at least in a stoichiometric amount with respect to the alkane impurities to be removed. More preferably, sulfur trioxide is employed in a stoichiometric excess with respect to said alkane impurities. The molar ratio between sulfur trioxide and the alkane impurities is particularly in a range of from 10:1 to 1:1, preferably 10:1 to 3:1.

According to the invention, an impure alkane, especially impure methane, is contacted with an active compound. Suitable active compounds are described in the aforementioned prior art documents relating to methods for the production of alkanesulfonic acids as initiators for said production of alkanesulfonic acids from alkanes and sulfur trioxide, namely WO 2015/071365 A1, WO 2015/071455 A1, WO 2018/096138 A1 and WO 2018/146153 A1. Furthermore, suitable initiators, which may be employed as active compounds in the sense of the present invention, are described in unpublished European patent application 18196493.3, unpublished European patent application 18157127.4 and unpublished European patent application 18196498.2, which are hereby fully incorporated by reference.

A suitable active compound may in general be a compound comprising a heterolytically cleavable bond between two atoms, each selected from the group consisting of nitrogen, phosphorus, sulphur and oxygen. Preferred are heterolytically cleavable peroxide compounds, but also for example heterolytically cleavable diazo compounds may be employed.

Preferably, the active compound is heterolytically cleavable under superacid conditions. The term superacid refers to an acid having a higher acid strength than sulfuric acid.

Suitable active compounds comprise inorganic or organic peroxoacids, which are stable at room temperature. Suitable inorganic peroxoacids comprise peroxoacids of boron, silicon, phosphorus, sulfur, nitrogen or carbon. The peroxoacids may be obtainable from a reaction of an oxoacid with a peroxide, especially hydrogen peroxide. Specific examples comprise the reaction product of phosphoric acid with hydrogen peroxide, the reaction product of boric acid with hydrogen peroxide and/or potassium peroxomonosulfate. Suitable organic peroxoacids comprise peroxoalkanesulfonic acids, peroxybenzoic acid and trifluoroperacetic acid.

In place of the free oxoacids or peroxoacids, salts thereof may also be employed.

The aforementioned compounds may be reacted with sulfur trioxide in order to form an active compound in the sense of the present invention.

More examples are described in the aforementioned prior art documents incorporated herein by reference. Every initiator suitable to be employed in the aforementioned methods of the prior art for the production of alkanesulfonic acids from alkanes and sulfur trioxide may be employed in the method of the present invention as an active compound.

In a preferred embodiment of the invention, the active compound corresponds to formula (I)

ALK-SO$_2$—O—O—X          (I)

wherein ALK is a branched or unbranched alkyl group, especially a methyl, ethyl, propyl, butyl, isopropyl, isobutyl group, or a higher alkyl group, an X=hydrogen, zinc, aluminium, an alkali or alkaline earth metal.

This active compound corresponds to a peroxoacid of an alkanesulfonic acid, which may also be a side-product of the inventive method. The active compound may, for example, be prepared by the reaction of the corresponding alkanesulfonic acid, especially methanesulfonic acid, with a peroxoacid or a peroxide, especially hydrogen peroxide. The active compound may be prepared separately in the peroxo form and subsequently be employed in the inventive method. Alternatively, the active compound may be prepared in situ. A precursor of the active compound may be prepared comprising a mixture of an alkanesulfonic acid, especially methanesulfonic acid, and a peroxide, especially hydrogen peroxide and said precursor may be added to the reaction mixture of the present invention. In a further alternative, an alkanesulfonic acid, especially methanesulfonic acid, and a peroxide, especially hydrogen peroxide, may be added separately to the reaction mixture and the active compound of formula (I) is produced in situ.

Alternatively, the active compound may for example correspond to formula (II)

ALK-SO$_2$—O—O—SO$_2$—X          (II)

wherein ALK is a branched or unbranched alkyl group, especially a methyl, ethyl, propyl, butyl, isopropyl, isobutyl group, or a higher alkyl group, an X=hydrogen, zinc, aluminium, an alkali or alkaline earth metal.

The compound of formula (II) may be obtained by reacting the compound of formula (I) with sulfur trioxide.

The initial molar ratio between the active compound and the impurities in the alkane to be purified is preferably in a range of from 1:1 to 1:3, particularly 1:2. However, in case the inventive method is performed in the presence of sulfur trioxide, the active compound may be regenerated by reaction with sulfur trioxide. In this case the active compound may be employed in catalytic amounts, particularly in a molar ratio of 1:50 to 1:10000, more preferably in the range of from 1:100 to 1:500, with respect to the sulfur trioxide present.

The inventive method is preferably performed at a pressure of from 1 to 200 bar, more preferably 10 to 150 bar, particularly 50 to 120, especially at a pressure of 100 bar.

The inventive method is preferably performed at a temperature of from 0° C. to 100° C., more preferably 20 to 60, particularly 20 to 55.

In a preferred embodiment of the invention, the impure alkane may be reacted with the active compound for a particular period of time in a batch reactor or the like. The reaction time is preferably in a range of from 5 minutes to 3 days, more preferably from 20 minutes to 24 hours, particularly 1 hour to 8 hours. A longer reaction time generally leads to a higher reduction of impurities. On the other hand, a longer reaction time leads to a larger amount of the desired alkane, especially methane, being reacted with the active compound.

FIG. 1 schematically depicts the inventive method showing a reactor for contacting an impure alkane with an active compound and educt and product flows.

The purified alkane is preferably produced in form of a gas. The gas may be separated from the reaction mixture by decompression of the reactor, for example from 100 bar to 95 bar. Furthermore, if the method is performed in the presence of sulfur trioxide, said sulfur trioxide may be removed by means of washing.

In an alternative embodiment of the invention, the purified alkane obtained after contacting the impure alkane, especially impure methane, with the active compound is again contacted with the active compound, optionally in the presence of sulfur trioxide. Effectively, by repeating the inventive method with the product of the inventive method, the amount of impurities may be reduced further. The inventive method may thus comprise multiple cycles of purification. The inventive method may be performed in multiple cycles by sequentially reacting an impure alkane with an active compound, optionally in the presence of sulfur trioxide in a cascade of batch reactors. Preferably, the impure alkane, especially impure methane, is reacted at least two, three, four, five, six, or more times. Particularly preferred are 4 to 5 cycles. Preferably, the number of cycles does not exceed 10. In each step, the product of the preceding step is employed and contacted with the active compound, optionally in the presence of sulfur trioxide. The product of a preceding step might be fully used in the subsequent step, or only a part of the product may be used in the subsequent step. A part of the product may also be recycled to a preceding step.

Alternatively, the impure alkane, especially methane, may be contacted with the active compound, optionally in the presence of sulfur trioxide, in a batch reactor for a reaction time as specified above. Subsequently, the purified alkane, especially purified methane, is isolated and further reaction products, such as alkanesulfonic acids are removed from the batch reactor. The purified alkane, especially purified methane, may then be fed back to the same batch reactor and again contacted with the active compound, optionally in the presence of sulfur trioxide. In this manner, the impure alkane, especially methane, may be repeatedly recycled until a desired degree of purification is achieved.

Furthermore, the inventive method may be carried out in a continuous reactor.

The inventive method may for example remove about half of the higher alkane impurities present in the impure alkane. For example, if impure methane comprising 0.025 vol % of ethane is employed, the amount of ethane may be reduced to 0.015 vol % after one purification cycle. With the inventive step, methane with a purity of 99.9999% may for example be produced.

In an alternative embodiment, the inventive method comprises the following steps:
i) providing the active compound;
ii) reacting the active compound with an impure alkane, especially impure methane, in a high-pressure autoclave or a laboratory reactor;
iii) setting a pressure of from 1 to 200 bar;
iv) optionally adding sulfur trioxide to the reactor;
v) controlling the temperature of the reaction mixture at 0° to 100° C.;
vi) optionally repeating steps i) to v) with the obtained purified alkane.

In an alternative embodiment, the object of the invention is solved by the above described inventive method for the purification of alkanes, especially methane, characterized by its use for the purification of alkanes, especially methane.

In an alternative embodiment, the object of the invention is solved by the use of sulfur trioxide in the purification of alkanes, especially methane. Sulfur trioxide may be used in the abovementioned inventive method. Particularly, sulfur trioxide is used in the purification of alkanes in the presence of an active compound as described above.

In an alternative embodiment, the object of the invention is solved by the use of an active compound as defined above in the purification of alkanes, especially methane. Particularly an active compound corresponding to formula (I)

ALK-SO$_2$—O—O—X    (I)

wherein ALK is a branched or unbranched alkyl group, especially a methyl, ethyl, propyl, butyl, isopropyl, isobutyl group, or a higher alkyl group, an X=hydrogen, zinc, aluminium, an alkali or alkaline earth metal, is used in the purification of alkanes, especially methane. The active compound is preferably present in a method, where an impure alkane, especially impure methane, is contacted with sulfur trioxide. Without the intention of being bound by theory, it is believed that the active compound, optionally after reacting with sulfur trioxide, reacts with impurities in the impure alkane, especially impurities in the form of higher alkanes, whereby for example the corresponding alkanesulfonic acid may be formed

EXAMPLE 1

In a 400 mL stainless steel high-pressure reactor, 245.02 g of fuming sulfuric acid (34.1%, 1.044 mol SO$_3$) was added using an HPLC pump while maintaining the temperature of the lines at 50° C. The reactor was heated to 50° C. with constant stirring speed of 1000 rpm. The active compound was prepared by dissolving 1.38 mL (21.25 mmol) of methanesulfonic acid (99.5%, BASF) in 12 mL (220.0 mmol) of sulfuric acid 98% (Analysis grade, Merck). This mixture was cooled down to 0° C. using an ice bath before dropwise addition of 464 μL (9.74 mmol) of hydrogen peroxide 60% (Arkema). Once the reactor reached 50° C., the vessel was pressurized with 92.6 bar (1.084 mol) of methane (99.5%, Air Liquide). The active compound was then injected into the reactor using an HPLC pump, raising the pressure inside the reactor to 97 bar. After 16 h, the pressure dropped to 31.8 bar, indicating that a large amount of methane was consumed. The reactor was then cooled down to room temperature, the excess pressure was removed to a set of scrubbers and the product (279.57 g) consisting of a slightly colorless liquid was stored in a glass bottle. The methane gas employed and the gas released from the reactor after the reaction was analysed by GC-MS. The purity of methane was increased from 99.9292% to 99.9559%, while at the same time ethane impurities were almost halved from 0.0708% to 0.0441%.

EXAMPLE 2

In a 300 ml autoclave, a mixture of 45.1 g of 65% (w/w) oleum, 23.02 g of H$_2$SO$_4$ and 20.1 g methanesulfonic acid is charged, and the temperature controlled to 50° C. After a constant pressure of 100 bar of methane gas (methane quality 98%, see table 1) was set, intensive stirring is performed with a Rhuston turbine stirrer. Now, 43.4 g (~23.6 ml) of an initiator solution consisting of 154.43 g 32% (w/w) oleum with 8.3 ml H$_2$O$_2$ (70% in water) is metered dropwise to the solution. Methane uptake (~7 NL) was observed throughout a period of ~4 h. The reactor was then cooled down to room temperature, the excess pressure was removed to a set of scrubbers and the product (125.45 g) consisting of a clear, slightly reddish liquid was stored in a glass bottle. The methane gas employed and the gas released from the reactor after the reaction was analysed by GC-MS. The purity of methane was increased from 97,949% to 99.18%, while at the same time ethane and higher alkane impurities were not detected anymore.

The yield is higher than 90%, based on sulfur trioxide. The reaction product contains 41% methanesulfonic acid.

TABLE 1

| component | employed gas composition mol [%] | Reaction gas composition mol [%] |
|---|---|---|
| Others (N2, CO2, ...) | 0.90 | 0.82 |
| propane | 0.25 | <100 ppm |
| ethan | 0.91 | <100 ppm |
| methan | 97.94 | 99.18 |

EXAMPLE 3

In a 300 ml autoclave, a mixture of 108.6 g of 65% (w/w) oleum, 41.5 g of H$_2$SO$_4$ and 41.5 g methanesulfonic acid is charged, and the temperature controlled to 50° C. After a constant pressure of 100 bar of methane gas (methane quality see table 2) was set, intensive stirring is performed with a Rhuston turbine stirrer. Now, 28.9 g (~15.7 ml) of an initiator solution consisting of 152.63 g 32% (w/w) oleum with 8.25 ml H$_2$O$_2$ (70% in water) is metered dropwise to the solution. Methane uptake (~7 NL) was observed throughout a period of ~4 h. The reactor was then cooled down to room temperature, the excess pressure was removed to a set of scrubbers and the product (236.00 g) consisting of a clear, slightly reddish liquid was stored in a glass bottle. The methane gas employed and the gas released from the reactor after the reaction was analysed by GC-MS. The purity of methane was increased from 99.61% to 99.67%, while at the same time ethane and higher alkane impurities were not detected anymore.

The yield is higher than 90%, based on sulfur trioxide. The reaction product contains 52.3% methanesulfonic acid.

TABLE 2

| component | employed gas composition mol [%] | Reaction gas composition mol [%] |
|---|---|---|
| Others (N2, CO2, ...) | 0.35 | 0.33 |
| ethane | 324 ppm | <100 ppm |
| methan | 99.62 | 99.67 |

The invention claimed is:
1. A method for the purification of methane, comprising contacting an impure methane with an active compound comprising a heterolytically cleavable bond between two atoms, each selected from the group consisting of nitrogen, phosphorus, sulphur and oxygen, wherein the active compound corresponds to formula (I)

ALK—SO$_2$—O—O—X    (I)

or formula (II)

ALK—SO$_2$—O—O—SO$_2$—X    (II)

wherein ALK is a branched or unbranched alkyl group,
X is hydrogen, zinc, aluminium, an alkali or alkaline earth metal, and
obtaining purified methane, wherein the impure methane is methane comprising higher alkane impurities.

2. The method according to claim 1, wherein the impure methane is contacted with the active compound in the presence of sulfur trioxide.

3. The method according to claim 1, wherein the impure methane is in a gaseous state.

4. The method according to claim 1, wherein the method is performed at a pressure of from 1 to 200 bar.

5. The method according to claim 1, wherein the method is performed at a temperature of from 0° C. to 100° C.

6. The method according to claim 1, wherein the purified methane obtained after contacting the impure methane with the active compound is again contacted with an active compound, optionally in the presence of sulfur trioxide.

7. The method according to claim 1, wherein the method is performed in a batch reactor within a reaction time of from 5 minutes to 3 days, or in a continuous reactor.

8. The method according to claim 1, comprising the following steps:
  i) providing the active compound;
  ii) reacting the active compound with an impure methane, in a high-pressure autoclave or a laboratory reactor;
  iii) setting a pressure of from 1 to 200 bar;
  iv) optionally adding sulfur trioxide to the reactor;
  v) controlling the temperature of the reaction mixture at 0° to 100° C.; and
  vi) optionally repeating steps i) to v) with the obtained purified methane.

9. The method according to claim 1, wherein the alkyl group is methyl, ethyl, propyl, butyl, isopropyl, an isobutyl group, or a higher alkyl group.

10. The method according to claim 1, wherein the method is performed at a pressure of from 50 to 120 bar.

11. The method according to claim 1, wherein the method is performed at a temperature of from 20° C. to 60° C.

* * * * *